US00PP29803P3

(12) United States Plant Patent
Yencho et al.

(10) Patent No.: US PP29,803 P3
(45) Date of Patent: Nov. 6, 2018

(54) SWEETPOTATO PLANT NAMED 'NCORNSP-020BWGWE'

(50) Latin Name: ***Ipomoea batatas* (L.) Lam.**
Varietal Denomination: NCORNSP-020BWGWE

(71) Applicant: North Carolina State University, Raleigh, NC (US)

(72) Inventors: George Craig Yencho, Raleigh, NC (US); Meri K. Reeber, Apex, NC (US); Kenneth Vincent Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 55 days.

(21) Appl. No.: 15/330,762

(22) Filed: Nov. 4, 2016

(65) Prior Publication Data

US 2018/0132402 P1 May 10, 2018

(51) Int. Cl.
*A01H 5/12* (2018.01)
*A01H 5/06* (2018.01)

(52) U.S. Cl.
USPC ..... Plt./258
CPC ..... *A01H 5/06* (2013.01); *A01H 5/12* (2013.01)

(58) Field of Classification Search
USPC ..... Plt./258
See application file for complete search history.

(56) References Cited

PUBLICATIONS

UPOV hit on ornamental sweet potato plant named, 'NCORNSP-020BWGWE' CA PBR 16-8968, application filing date Jul. 8, 2016.*

* cited by examiner

*Primary Examiner* — Anne Marie Grunberg
(74) *Attorney, Agent, or Firm* — Myers Bigel, P.A.

(57) ABSTRACT

'NCORNSP-020BWGWE' is a compact, non-twining, upright variety producing many short shoots. It is distinguishable from other cultivars by its yellow green heart shaped leaves with dentate to serrate irregular projecting points (i.e. teeth) with a cordate-deltoid base; a compact habit and erect mounding plant architecture. The lime green, toothed leaves of this plant, short internodes, and the plant architecture are what makes 'NCORNSP-020BWGWE' unique amongst the current ornamental sweetpotatoes in the marketplace. 'NCORNSP-020BWGWE' also exhibits very good vigor and is very well branched. In greenhouse and field trials conducted since 2013, 'NCORNSP-020BWGWE' has been shown to be much less vigorous than *Ipomoea batatas* 'Margarita' and 'Blackie' and is suitable for use as a landscape or containerized plant. The production of flowers by 'NCORNSP-020BWGWE' is sporadic under short day conditions.

4 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-020BWGWE'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato (OSP) plants are a heat-loving, drought-tolerant, perennial vine typically grown as an annual. However, ornamental sweetpotato plants are distinguished from the edible cultivated forms in that they possess unique foliage colors, leaf shapes, and growth habits, giving them significant value in the ornamental marketplace.

Ornamental sweetpotatoes are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes continue to grow throughout the entire growing season and require little maintenance. Moreover, these plants have few insect or disease problems.

To meet the growing horticultural demand for ornamental sweetpotatoes (OSP), it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth habit that do not out-compete other species in mixed containers.

'NCORNSP-020BWGWE' was bred to meet the increasing demand for new ornamental sweetpotatoes. 'NCORNSP-020BWGWE' is a compact, non-twining, upright variety producing many short shoots. It is distinguishable from other cultivars by its yellow green heart shaped leaves with dentate to serrate irregular projecting points (i.e. teeth) with a cordate-deltoid base; a compact habit and erect mounding plant architecture. The lime green, toothed leaves of this plant, short internodes, and the plant architecture are what makes 'NCORNSP-020BWGWE' unique amongst the current ornamental sweetpotatoes in the marketplace. 'NCORNSP-020BWGWE' also exhibits very good vigor and is very well branched. In greenhouse and field trials conducted since 2013, 'NCORNSP-020BWGWE' has been shown to be much less vigorous than the *Ipomoea batatas* OSP 'Margarita' (unpatented) and 'Blackie' (unpatented) and is suitable for use as a landscape or containerized plant. The production of flowers by 'NCORNSP-020BWGWE' is sporadic under short day conditions.

Lineage. 'NCORNSP-020BWGWE' (breeding designation NC8397-049ORN) originated from a conventional cross between the proprietary *Ipomoea batatas* OSP breeding lines NC8148-006ORN (the female parent; not patented) and NC8124-001ORN (the male parent; not patented). Botanical seed was harvested from this and other ornamental sweetpotato clones planted in our winter greenhouse-crossing block between September of 2012 and March of 2013 in Raleigh, N.C. NC8148-006ORN resulted from a conventional cross between the proprietary *Ipomoea batatas* OSP breeding lines NC7124-014ORN (the female parent; not patented) and NC7051-001RN (the male parent; not patented). NC8124-001ORN resulted from a cross between the proprietary *Ipomoea batatas* OSP breeding lines NC6938-001ORN (the female parent; not patented) and NC7518-002ORN (the male parent; not patented). Botanical seed from this family was planted in the greenhouse in February 2013. The first cycle of selection on the population was exercised in the seedling trays and survivors were transferred to a single 6-inch pot, which was then maintained in the greenhouse. Cuttings (2 each) were taken from the plants in April and planted in the field as 2-plant unreplicated plots during mid-June 2010. The single, individual plant now known as 'NCORNSP-020BWGWE' was selected Sep. 3, 2013 based on its combination of exceptional features, and has been propagated asexually since that time.

Asexual Reproduction. Since its selection, *Ipomoea batatas* 'NCORNSP-020BWGWE' has been asexually reproduced in North Carolina predominantly by vegetative propagation of vine cuttings. Successively, there have been four cycles of vegetative propagation, one cycle of tissue culture micropropagation, and multiple vegetative propagation cycles to increase the plant population. Asexual reproduction of 'NCORNSP-020BWGWE' by cuttings has shown that the unique features of the new cultivar are stable and the plant reproduces true to type in successive generations.

SUMMARY OF THE INVENTION

'NCORNSP-020BWGWE' is a compact, non-twining, upright variety producing many short shoots. It is distinguishable from other cultivars by its yellow green heart shaped leaves with dentate to serrate irregular projecting points (i.e. teeth) with a cordate-deltoid base; a compact habit and erect mounding plant architecture. The lime green, toothed leaves of this plant, short internodes, and the plant architecture are what makes 'NCORNSP-020BWGWE' unique amongst the current ornamental sweetpotatoes in the marketplace. 'NCORNSP-020BWGWE' also exhibits very good vigor and is very well branched. In greenhouse and field trials conducted since 2013 by the breeding program and industry collaborators 'NCORNSP-020BWGWE' has been shown to be much less vigorous than *Ipomoea batatas* 'Margarita' and 'Blackie' and is suitable for use as a landscape or containerized plant. The production of flowers by 'NCORNSP-020BWGWE' sporadic under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION OF THE NEW VARIETY

The following is a detailed description of the botanical characteristics of a new and distinct cultivar of *Ipomoea batatas* plant known by the cultivar name 'NCORNSP-020BWGWE'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions reported herein are from a group of 50-day-old specimens grown individually in six-inch azalea pots. The plants were grown in Raleigh, N.C., under commercial practice in a glass-covered greenhouse, where, during the fall, day and night temperatures range between 30-40° C. and 22-26° C., respectively. After rooting, plants were treated with 200 ppm 20-10-20 fertilizer daily. Plant measurements were taken in November 2015 in Raleigh, N.C. *Ipomoea batatas* 'NCORNSP-020BWGWE' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-020BWGWE'.

Growth conditions: *Ipomoea batatas* 'NCORNSP-020BWGWE' has very good vigor and a moderate growth rate. In locales with mild winter conditions, *Ipomoea batatas* 'NCORNSP-020BWGWE' will grow perennially; otherwise it is an annual plant. Similar to other cultivated sweetpotatoes, wind or rain rarely causes much damage to 'NCORNSP-020BWGWE', but if damage does occur, the plant drops the damaged leaves and grows new shoots at nodes where the leaves were lost. Under low light levels in a greenhouse, 'NCORNSP-020BWGWE' can develop intumescence, which will remain on the affected foliage, but will be outgrown with new foliage.

Figure 1:
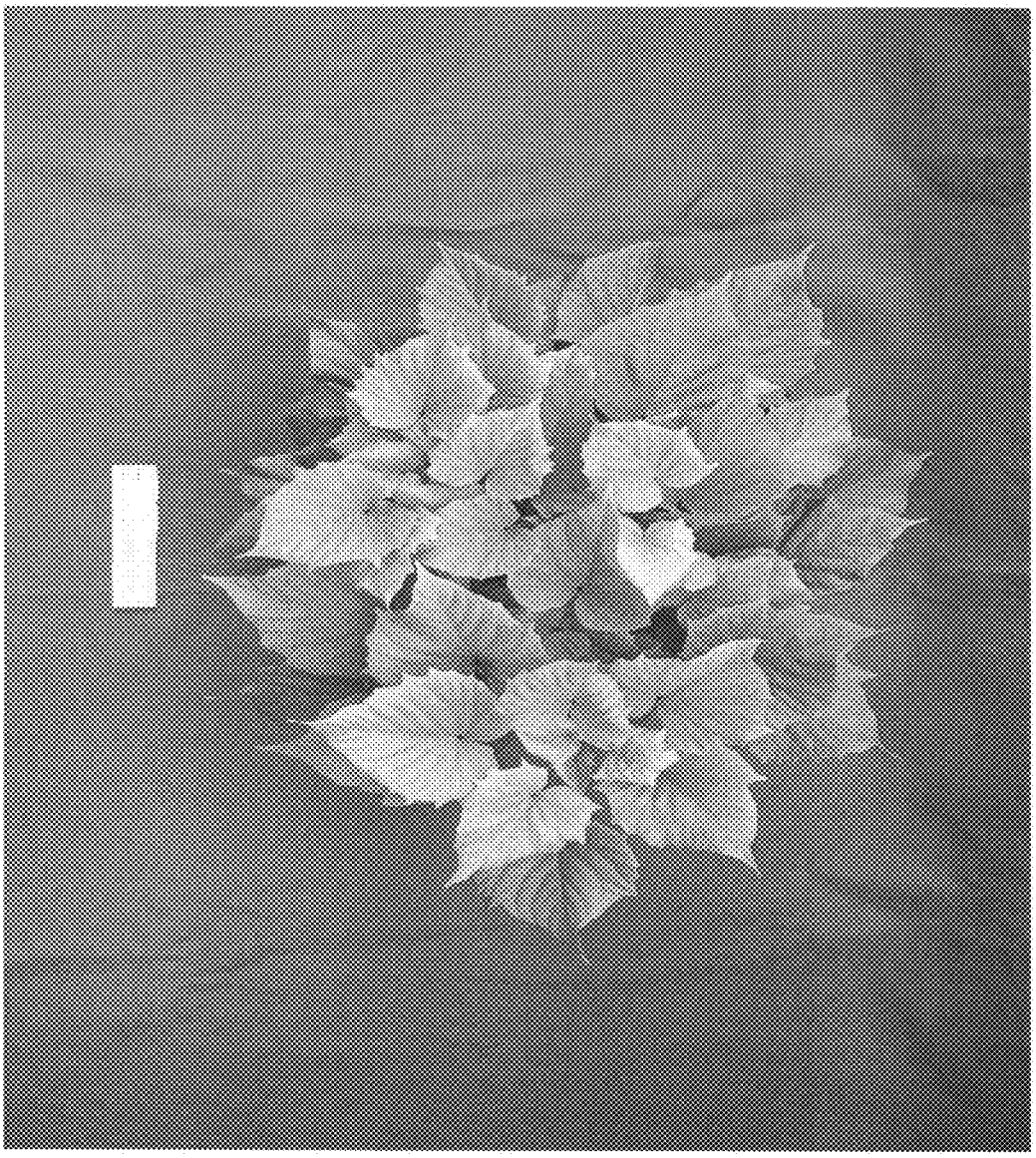
FIG. 1 is a color photograph of a typical specimen of greenhouse grown *Ipomoea batatas* 'NCORNSP-020BWGWE' in a 6-inch pot from the top, 50 days after planting.
Figure 2:
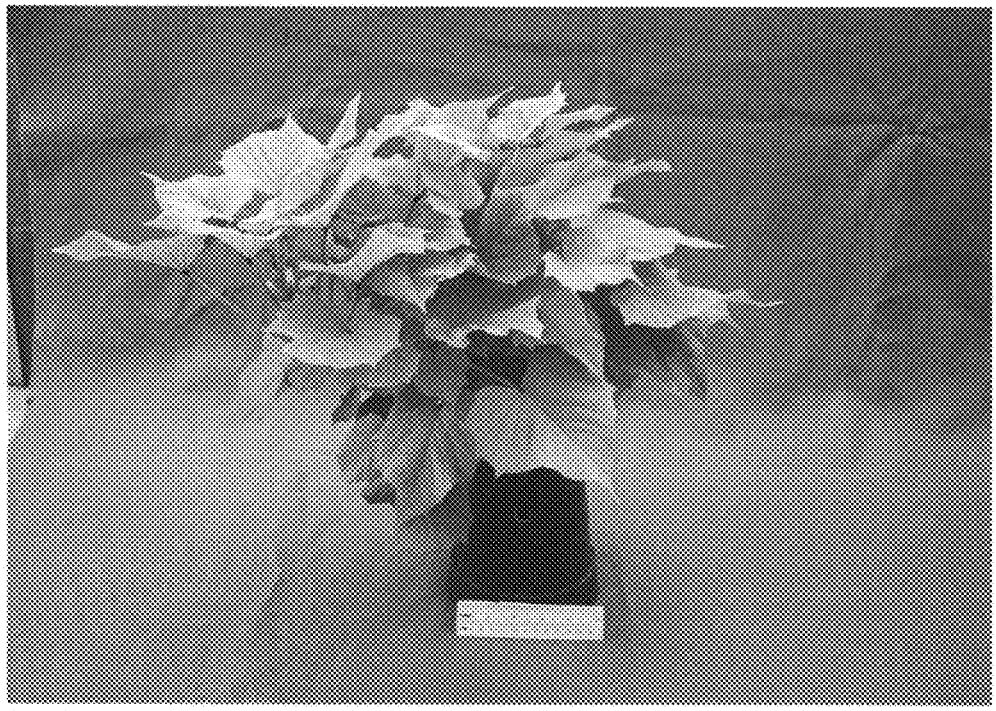
FIG. 2 is a color photograph of a typical specimen of *Ipomoea batatas* 'NCORNSP-020BWGWE' in a 6-inch pot from the side, 50 days after planting.
Figure 3:
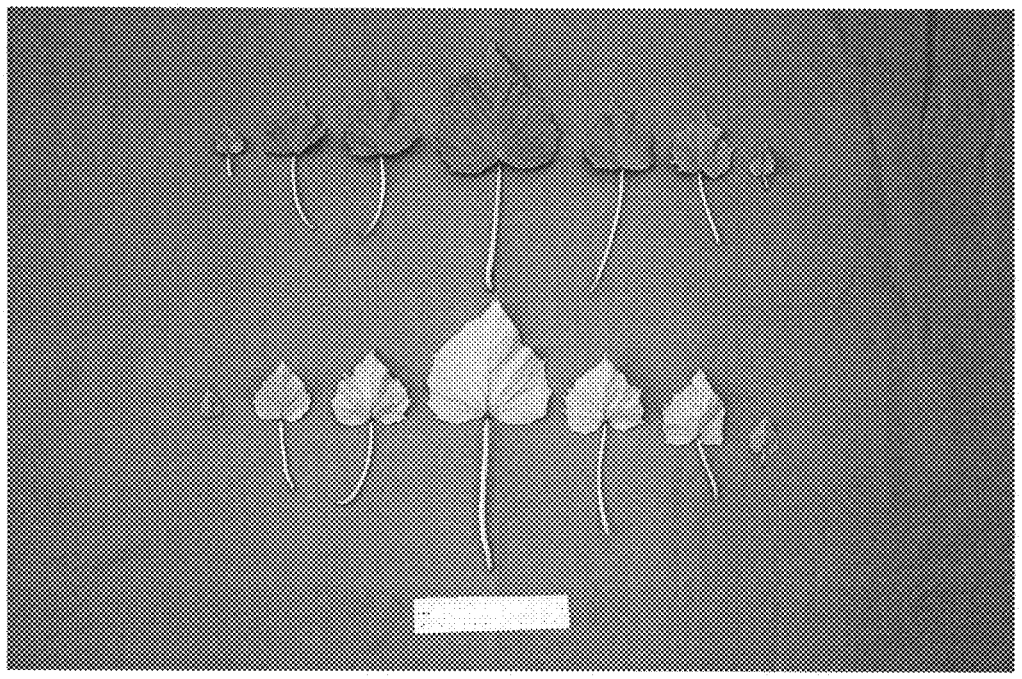
FIG. 3 is a color photograph showing the variety of leaves produced by *Ipomoea batatas* 'NCORNSP-020BWGWE' and the lower surface of the leaf (bottom row), 50 days after planting.
Figure 4:
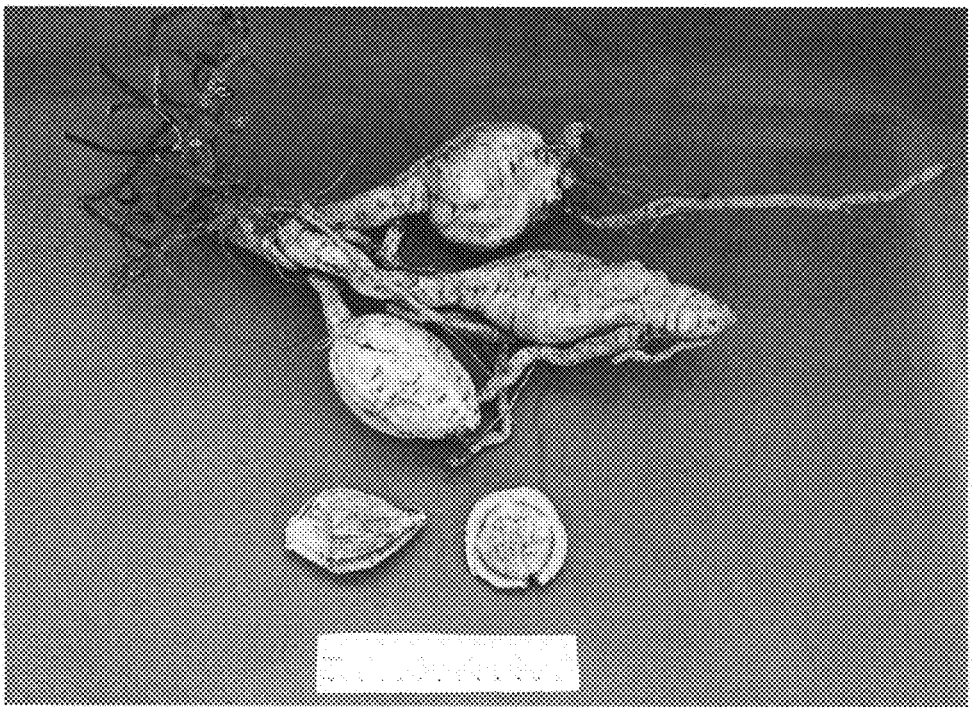
FIG. 4 is a color photograph showing the variety of roots produced by *Ipomoea batatas* 'NCORNSP-020BWGWE' in the field, 115 days after planting.

Aboveground structure and coloration: FIGS. 1, 2, 3, and 4 show the shape and coloration of a typical specimen of *Ipomoea batatas* 'NCORNSP-020BWGWE'. Color may vary somewhat in response to temperature and nutrient stress. Overall, this cultivar is a compact, non-twining, upright herbaceous plant that has an average height of ~25.1 cm and an average area spread of ~53.2 cm. The growth habit of this plant is to grow upright with shoots growing upward and outward.

Branches:

*Branching habitat.*—Freely-branching with ~3-4 primary lateral branches coming off the stem. Very dense foliage and no pinching is required to stimulate branching. Branch texture is glabrous with slight pubescence.

*Vegetative lateral branching.*—Length: ~33.7 cm. Diameter: ~0.7 cm. Internodes are short with an average length of ~1.4 cm.

*Secondary lateral shoots.*—Many lateral branches are formed and each axil has latent shoots. Length: ~13.1 cm. Diameter: ~0.5 cm. Internodes are short with an average length of ~1.6 cm.

*Stem.*—Round and smooth with an upward, outward, and slightly undulating aspect and very strong, slightly flexible, non-brittle strength. Color: Yellow green (RHS 144A-144B) with purple (RHS N77A) at petiole junction.

*Adventitious roots.*—Present at nodes. Color: purple (RHS N77A) with yellow green (RHS 44B-C).

*Petiole.*—Petioles are held upward and display the leaf slightly vertical with a slight twisting. Leaf petiole has a smooth texture with a matte finish and slight pubescence. Length: ~14.5 cm. Diameter: ~0.5 cm. Color: Yellow green (RHS 144B-144C) with purple (RHS N77A) on young leaves at leaf petiole junction.

Foliage: Leaves are alternate and tend to slightly spiral around the stem. They are deltoid to slightly cordate with dentate to serrate irregular projecting points (i.e. teeth). Leaves have 0 lobes per leaf. Leaf shape is somewhat variable as is size (see FIG. 3).

*Quantity.*—Heavily foliated, with ~34 leaves per lateral branch.

*Mature leaf length.*—~13.6 cm.

*Mature leaf width.*—~12.6 cm.

*Leaf margin.*—Dentate to serrate irregular projecting points (i.e. teeth).

*Leaf apex.*—Deltoid and acute.

*Leaf base.*—Deltoid to slightly cordate.

*Leaf texture.*—Glabrous texture and matte finish.

*Venation.*—Pinnate to cross-venulate. Texture: Glabrous.

*Color.*—Leaves are yellow green and range within that palette as they mature. See also Table 1.

TABLE 1

Leaf color of *Ipoinoea batatas* 'NCORNSP-020BWGWE'.

| Leaf Structure | Upper Surface | Lower Surface |
|---|---|---|
| Young Leaf | Yellow Green (RHS144B-C) | Greyed Yellow Green (RHS 144B-C) |
| Mature Leaf | Yellow Green (RHS 144A) | Green (RHS 138C-143D) |
| Vein-mature leaf | Yellow Green (RH5144A) with Purple (RHS N77A) at petiole junction | Yellow Green (RHS144A) with Purple (RHS N77A fading to RHS N77B) from petiole junction to center of leaf |
| Vein-young leaf | Yellow Green (RHS144B) | Yellow Green (RHS 144B-C) with Purple (RHS N77A fading to RHS N77B) at petiole junction to center of leaf |

Inflorescence: Flowers sporadically throughout the season in response to a variety of stressful conditions (e.g., drought, nutrient stress, cloudy weather). Shorter day lengths enhance flowering, but the precise photoperiod for flower induction is currently unknown. Solitary, regular funnel-form flowers arising from leaf axils on secondary lateral branches are formed. Peduncles are yellow green (RHS 144B) with purple (RHS N79A) at the stem-peduncle junction and have a smooth texture. Peduncle length: ~4.4 cm, peduncle width: ~0.4 cm. Flower buds are pale purple (RHS 76B-76D) and elliptic. Flower bud length: ~2.3 cm, flower bud width: ~0.6 cm. Corolla width: ~4.8 cm, corolla length: ~4.7 cm. Limb color: Light purple (RHS 76D) on the outer surface and light purple (RHS 76C-76D) on the inner surface. The inner throat color gets lighter from base to limb going from purple (RHS 77A) at the base to light purple (RHS 76C-76D) near the limb. The limb is pentagonal with slight fragrance. The flower averages five sepals. Occasionally, the flower will produce six sepals. The two outer sepals are shorter than the inner sepals. Average sepal length: ~1.0 cm, average sepal width: ~0.3 cm. The sepals are obovate with a caudate apex and are yellow green (RHS N144A with 144B) in color. Sepal texture is glabrous on both the upper and lower surface. A single pistil consists of one style and one stigma ~2 cm in length. Stigma and style are both cream (RHS 157A). The stigma is slightly exerted relative to the stamens. The ovary is light yellow (RHS 154A) and superior with two locules that contain one or two ovules. At the base of the ovary are orange basal glands (RHS 163A) containing nectar, which cover the ovary. The flower averages five stamens. Occasionally, the flower will produce six stamens. Each stamen consists of a single cream-light pink filament averaging 1.5 cm in length topped with a single cream-white anther averaging ~0.3 cm in length. Filament color: cream-light pink (RHS N155B-N79B). Anther color: cream (RHS 155A). Pollen color: cream (RHS 155A). Pollen amount is profuse. Fruit has not been observed under normal greenhouse conditions.

Storage root coloration: Plants form no, to small, underground storage roots that are occasionally malformed and do not meet USDA Sweetpotato Storage Root Grade Standards (see FIG. 4). Fibrous roots are typically cream (RHS 155B). Storage roots that are formed possess greyed yellow (RHS 161C-161D) skin with hints of purple (RHS 76D) and a greyed yellow flesh (RHS 162B-162A) with some purple (RHS N79A-N79C).

Disease or pest resistance: 'NCORNSP-020BWGWE' is susceptible to whiteflies and thrips in a greenhouse environment. 'NCORNSP-020BWGWE' is susceptible to damage by Japanese beetles under outdoor conditions. The susceptibility of 'NCORNSP-020BWGWE' to other known insects and pathogens of sweetpotato is unknown. Under low light conditions, slight edema may occur.

Comparison with parent plants and other *Ipomoea batatas* cultivars. 'NCORNSP-020BWGWE' is very distinct based on leaf shape and plant architecture. 'NCORNSP-020BWGWE' originated from a cross between the proprietary *Ipomoea batatas* OSP breeding lines NC8148-006ORN (the female parent; not patented) and NC8124-001ORN (the male parent; not patented). NC8148-006ORN, the female parent, has yellow-green foliage, and cordate leaves with no to slight leaf margin toothing, while NC8124-001ORN has yellow-green foliage, and reniform leaves with strong leaf margin toothing, compared to 'NCORNSP-020BWGWE', which has yellow to yellow-green foliage and cordate leaves with strong toothing. Of the common cultivars of ornamental sweetpotato, 'NCORNSP-020BWGWE' is best compared with 'NCORNSP-019SCSHLM' (U.S. Plant Pat. No. 28,318) and 'Sweet Caroline Bewitched Imp' (U.S. Plant Pat. No. 23,651) cultivars (Table 2). Like 'NCORNSP-019SC-SHLM', 'NCORNSP-020BWGWE' has yellow green leaves. However, the leaves of 'NCORNSP-020BWGWE' are deltoid to slightly cordate with dentate to serrate irregular projecting points (i.e. teeth) compared to those of 'NCORNSP-019SCSHLM', which are entire with a cordate base. 'Sweet Caroline Bewitched Imp' has purple leaves, which are slightly lobed and toothed with a reniform-cordate base.

'NCORNSP-020BWGWE' has a compact, upright, non-twining plant habit compared with the moderately compact to compact, upright plant habit of 'NCORNSP-019SC-SHLM' and the compact, upright, non-twining habit of 'Sweet Caroline Bewitched Imp'. Furthermore, 'NCORNSP-020BWGWE' has a larger average leaf size compared with the smaller leaves of 'NCORNSP-019SC-SHLM'. Unlike 'Sweet Caroline Bewitched Imp', which does not produce flowers, even under short-day conditions, 'NCORNSP-020BWGWE' will flower sporadically throughout the season.

TABLE 2

Comparison of 'NCORNSP-020BWGWE' with other *Ipomoea batatas* cultivars.

| Characteristic | 'NCORNSP-020BWGWE' | 'NCORNSP-019SCSHLM' | 'Sweet Caroline Bewitched imp' |
|---|---|---|---|
| Plant Habit | Compact, Non-Twining, Upright | Moderately Compact to Compact, Upright | Compact, Non-Twining, Upright |
| Average Leaf Length and Width | Length: 13.6 Width: 12.6 | Length: 8.5 cm Width: 6.6 cm | Length: 12.1 cm Width: 13.6 cm |
| Foliage Color | Yellow green (RHS 144A) with purple (RHS N77A-N77B) at petiole junction and along midrib | Yellow green (RHS 144A-144B) with yellow green (RHS 144C-147D) venation | Dark greyed purple (RHS N186B) with dark greyed purple (RHS 187A) venation |
| Leaf Shape | Dentate to serrate teeth. Deltoid-slightly cordate with cordate-deltoid base | Entire. Cordate with cordate base | Slightly lobed to toothed. Cordate with reniform-cordate base |

We claim:

1. A new and distinct cultivar of *Ipomoea batatas* plant named 'NCORNSP-020BWGWE', substantially as illustrated and described herein.

* * * * *